United States Patent
Rohner et al.

(10) Patent No.: US 6,180,922 B1
(45) Date of Patent: Jan. 30, 2001

(54) FURNACE FOR PRODUCING DENTAL PROSTHESIS

(75) Inventors: Gottfried Rohner, Altstatten (CH); Johannes Lorunser, Bludenz (AT); Horst Ulbricht, Eschen (LI)

(73) Assignee: Ivoclar A.G., Schaan (LI)

( * ) Notice: Under 35 U.S.C. 154(b), the term of this patent shall be extended for 0 days.

(21) Appl. No.: 09/391,708

(22) Filed: Sep. 8, 1999

Related U.S. Application Data

(60) Provisional application No. 60/108,098, filed on Nov. 12, 1998.

(30) Foreign Application Priority Data

Sep. 25, 1998 (DE) .............................................. 198 44 136

(51) Int. Cl.⁷ ...................................................... F27B 5/14
(52) U.S. Cl. .......................... 219/390; 219/393; 433/25; 433/32
(58) Field of Search .................................. 219/393, 390; 433/25, 32, 218, 219, 223, 227; 72/57, 60

(56) References Cited

FOREIGN PATENT DOCUMENTS 664133    8/1938   (DE) .

*Primary Examiner*—Teresa Walberg
*Assistant Examiner*—Shawntina L. Fuqua
(74) *Attorney, Agent, or Firm*—John C. Thompson; Alan S. Korman

(57) ABSTRACT

A muffle furnace for producing dental prosthesis has a muffle into which dental material is placed and a drive to which a piston is connected. The piston is moveable by the drive into the muffle to apply pressure onto the dental material. A pressure sensing device for measuring pressure applied to the dental material is provided. The pressure sensing device has a pressure sensor and a deformation member having a first side and a second side. The first side of the deformation member is subjected to a counter force of the piston and the second side of the deformation member is fixedly attached to the muffle furnace.

30 Claims, 3 Drawing Sheets

FURNACE FOR PRODUCING DENTAL PROSTHESIS

This application claims benefit of U.S. Provisional application Ser. No. 60/108,098, filed Nov. 12, 1998.

BACKGROUND OF THE INVENTION

The present invention relates to a furnace for producing dental prostheses with a muffle, whereby the furnace comprises a piston driven by a drive which can be introduced into the muffle for exerting pressure onto the dental material, whereby a pressure sensor for detecting the pressure exerted by the piston is provided.

Furnaces for producing dental prostheses or dental replacement parts comprised of dental materials, especially dental ceramics, have been known for a long period of time. A plunger-type piston applies pressure onto the dental material positioned in the muffle whereby the muffle together with at least the lower portion of the piston is heated in the furnace. The furnace heats the muffle and thus the dental material for such a length of time until the dental material, under pressure applied by the piston, has completely filled the voids present in the muffle for producing the dental prostheses.

From German Patent 664 133 it is known that the inclusion formation of bubbles can be avoided when pressure is applied for an extended period of time.

The drive of the piston can be provided either by weight application or pneumatically or electrically with corresponding drive devices. For providing a cycle time as short as possible, while preventing inclusion of bubbles, it is favorable when the advancing speed of the piston is controllable. In this respect, pneumatically or electrically driven drive devices have been successfully used.

Different types of such furnaces are known. It has also been suggested already to provide an electric pressure cylinder design for driving the piston. For detecting the working pressure of the piston, the current uptake of the drive motor for the corresponding drive spindle is employed whereby, in addition, a travel/time measurement is carried out.

It is an object of the present invention to improve a muffle furnace of the aforementioned kind such that, while preventing bubble inclusion, an improved product quality of the aforementioned dental prostheses is ensured.

SUMMARY OF THE INVENTION

This object is inventively solved in that the pressure sensing device comprises a deformation member that is loaded at one side, especially at the rear end of the piston with respect to the muffle, by a counter force of the piston and is supported with its other side at the muffle furnace.

The inventive measures, i.e., loading one side of the pressure sensing device with a counter force of the piston, take into account especially the elasticity of the piston, which, when employing travel measurement, remains unaccounted for, for the control function, respectively, the desired control parameters. Surprisingly, a very precise observation of the operating perimeters of the furnace and of the piston can be ensured. The inventive solution detects exactly the pressure forces acting within the piston whereby it is essential that the entire load of the piston is taken into consideration for computation.

In a preferred embodiment of the inventive furnace, a deformation member, which is especially made of metal, is positioned between the rear end of the drive and a support provided at the muffle furnace. This embodiment allows a realization of the pressure sensing device that is not prone to fatigue or aging.

In a further preferred embodiment of the invention, the pressure sensing device is arranged between the end of the piston, which is remote from the pressure-applying end of the piston, or the drive provided thereat and a counter plate. The drive is provided between the piston and the counter plate and is preferably a step motor. The entire force which is produced by the drive is then received by the counter plate and introduced into the pressure sensing device which is secured by pull elements that are connected to the bottom plate of the muffle.

Thus, a closed force circuit is provided. It is understood that the pressure force of the piston is distributed onto all employed pull elements. Inventively, it is especially favorable when the pressure sensing device is arranged coaxially so that angular deviations are compensated or arranged.

In another preferred embodiment, a homogenous rubber plate is provided as the deformation member. It supports one of the sensor elements while the other sensor element is supported at the sensor plate.

In this embodiment, a defined portion of the force produced by the drive can be detected by the pressure sensor whereby this portion corresponds to the surface area occupied by the pressure sensor at the surface area of the deformation element.

When, for example, a maximum force of 300 N is produced by the drive, a precision pressure sensor with a measuring range of 30 N can be employed which takes up a surface area of $1/10$ of the total surface area of the deformation member.

It is especially preferred to provide a drive comprising a step motor and to preassemble the drive as a complete drive unit. When needed, the preassembled unit is attached by an adapter to already existing furnaces for improving the manufacturing precision. The preassembled drive unit allows to adjust the initial pressure exerted on the deformation member to such a low level that it remains, for example, under half the measuring precision of the pressure sensor. When the measuring precision of the pressure sensor is, for example, 0.2%, and when the maximum force to be applied by the piston is 300 N, the initial securing force which acts on the deformation member can be adjusted such that it does not surpass 3 N. In this manner, on the one hand, a safe securing action is ensured and, on the other hand, it is ensured that no measurable false readings are produced by mounting the drive unit.

Even though, in principle, a controlled dc motor for providing the drive force can be used, it is preferred to employ a step motor. It comprises preferably a threaded spindle which is a unitary part of the drive axle and supports a threaded sleeve. The threaded sleeve transforms the rotational movement into a linear movement in accordance with the pitch of the thread. It is understood that a rotational stop is provided which prevents rotation of the threaded sleeve. Such a rotational stop can be, for example, positioned with minimal play at one of the pull elements and can be embodied as a stop that acts in both rotational directions. Such a stop, in a modified embodiment, can also serve as a base for providing a travel sensor. For this purpose, the stop can either be coupled to a potentiometer slide or can provide an optical means that indicates the exact position of the piston by a binary code.

Surprisingly, the inventive coaxially arranged drive exhibits a substantially improved driving precision, especially in comparison to a pneumatic drive or a drive with a motor that acts on a toothed piston rod. The axial force application direction eliminates angular errors and the resulting frictional losses, respectively, reduces frictional losses to a neglectable magnitude.

It is especially advantageous that for a complete pressing of the material into the muffle voids, no air buffers are present so that the drive system has a very minimal elasticity coefficient. When employing a step motor as the drive, each individual step of the motor provides a substantial increase of the drive force. The travel/force characteristic line of the inventive furnace is thus advantageously suddenly very steep so that an instant detection of the end of the pressing step can be realized.

In this context it is especially advantageous that, inventively, the end of firing within the furnace can be coupled to an exact point in time which is defined by the end of the pressing step. After completion of a programed, advantageously fixedly adjusted post-pressing period, in an advantageous embodiment the electrically driven pivot mechanism of the furnace cover can be pivoted so that the muffle can be automatically and quickly cooled by opening automatically the furnace chamber.

This embodiment of the furnace is especially advantageous for firing lithium disilicate glass ceramics which exhibit a very strong reaction with the embedding material in the hot state of the embedding material. The intensity of the reaction directly depends on the exposure time and is accordingly substantially reduced when the end of the firing process can be detected and a cooling process can be automatically started.

This solution provides an especially advantageous progress with respect to conventional solutions in which a time control was used and the end of the pressing step could not be detected within a time period of less than three minutes. The inventive solution thus allows to reduce the processing time by up to three minutes.

According to a further especially advantageous aspect of the invention, the inventive solution may eliminate a subsequent etching with acid such as HF so that the respective manufacturing time period is no longer needed and a more precise fitting of the dental prostheses can be achieved.

Inventively, it is further advantageous to adapt the advancing speed of the piston with respect to the speed as well as the force so that an optimized adaptation to the specified pressing and firing task can be performed. In a preferred embodiment a constant force, for example, 250 N is first applied and a constant speed results in an increase of the force whereby reaching of the maximum set-point driving force coincides with the end of the pressing step.

With a programable adaptation to different viscosities but also to different reactivity in regard to the embedding material, the different types of glass ceramic materials can be taken into account. It is also possible by providing free programing to adapt the inventive furnace to currently unknown materials of the future so that respective pressing steps can be provided and optimized for such materials.

It is especially advantageous that the preferred embodiment of embodying the drive as a step motor, in combination with the inventive pressure sensing device, prevents overloading of the step motor and thus the loss of steps. The pressure sensing device controls the step motor such that no overload can occur so that the advancing travel for the pressing step always corresponds to the preset values and the step motor operates within safe limits without requiring additional travel sensors.

It is especially advantageous that the inventive furnace allows to considerably shorten the exposure time of the ceramic to be pressed in the embedding mass. The switch off criteria can be precisely determined and it is also possible to employ ceramics with fine channels having inherently a higher flow resistance. By shortening the exposure time, the reaction between the ceramic to be pressed and the embedding material can be greatly reduced or prevented so that new high-quality materials which are comparatively reactive can be employed as a ceramic to be pressed. The invention can also be safely used for fine dental bridge parts due to the slow force build-up during pressing.

A further advantage of the inventively improved switch-off criteria is the shortening of the pressing step so that the productivity of the inventive furnace in comparison to those of the prior art is improved. Furthermore, the manufacturing precision is improved when etching of the dental prostheses is no longer needed and the surface of the dental prostheses is more smooth and more visually pleasing.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 though 4.

Figure 1:
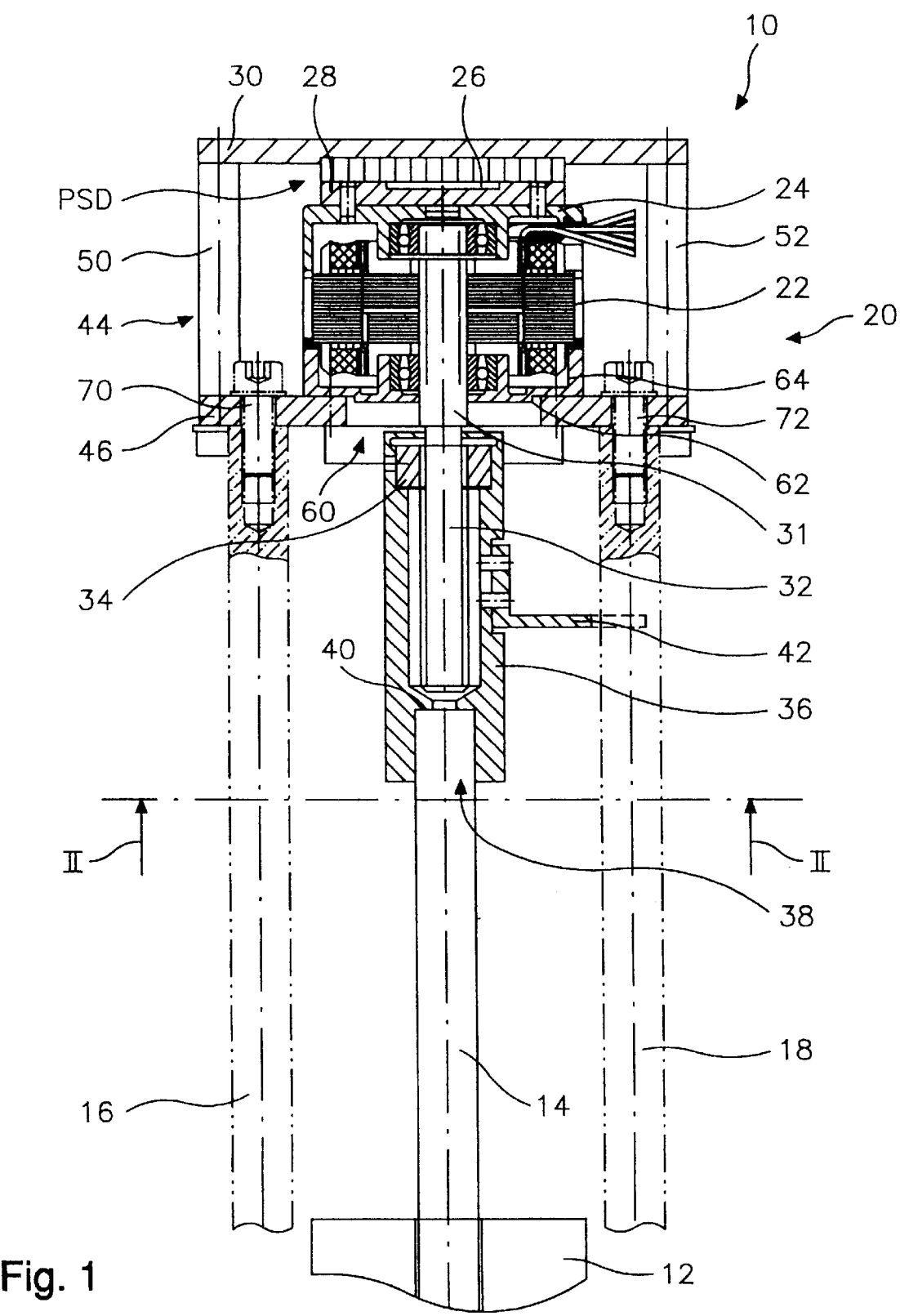
FIG. 1 shows a view of a portion of the inventive furnace, showing partly in section the drive and the pressure sensing device.

The embodiment of the inventive furnace 10 represented in FIG. 1 has a muffle 12 which is covered in a well-known manner by a hood.

A piston 14 and, in the shown embodiment, pull elements 16 and 18 extend through the hood whereby, according to a modified embodiment, it is suggested that the pull elements 16 and 18 extend external to the hood to a non-represented bottom plate on which the muffle with the dental material can be placed.

The furnace hood can be heated by known means and melting of the dental material allows movement of the piston 14 in the downward direction so that the dental material can fill the hollow spaces or voids of the muffle for forming the dental prostheses.

The piston 14 is connected axially to a drive 20 which comprises a step motor 22. The step motor 22 is supported at the side facing away from the piston 14 on a sensor plate 24 of a pressure sensing device PSD. The sensor plate 24 supports a pressure sensor 26. The pressure sensor 26 rests together with a sensor plate 24 at a deformation member 28 which is preferably a rubber or silicone plate. The deformation member 28 is supported in the upward direction across its entire surface area at a support plate 30 which is connected fixedly to the pull elements 16 and 18.

The step motor 22 comprises a shaft 31 which is an integral part of a drive spindle 32. A nut 34 is connected to the drive spindle 32 which is fixedly connected to a sleeve 36. The sleeve 36 thus functions as a threaded sleeve. According to another embodiment, it is suggested to provide the sleeve itself with a corresponding inner thread and to turn the sleeve downward of the inner thread to produce a blind bore.

Both embodiments have in common that independent of the position of the sleeve 36 relative to the drive spindle 32 the engagement area, i.e., the axial length along which the threaded engagement between drive spindle 32 and sleeve is realized, is identical. Accordingly, the frictional drive forces are also identical so that the step motor substantially can be actuated with the same drive currents and thus no additional non-linearity is introduced.

The sleeve 36 receives in the receiving opening 38 the piston 14. The piston 14 is received without play whereby optionally for facilitating insertion an insertion slant (not represented in FIG. 1) may be provided. It is especially preferred that the end face 40 of the piston 14 which is opposite the acting end (pressure-applying end) of the piston is supported over a large surface area in order to avoid deformation of the sleeve 36 and the piston 14.

The piston 14 is preferably comprised of a ceramic material while the sleeve 36, for example, is comprised of stainless steel.

Figure 2:
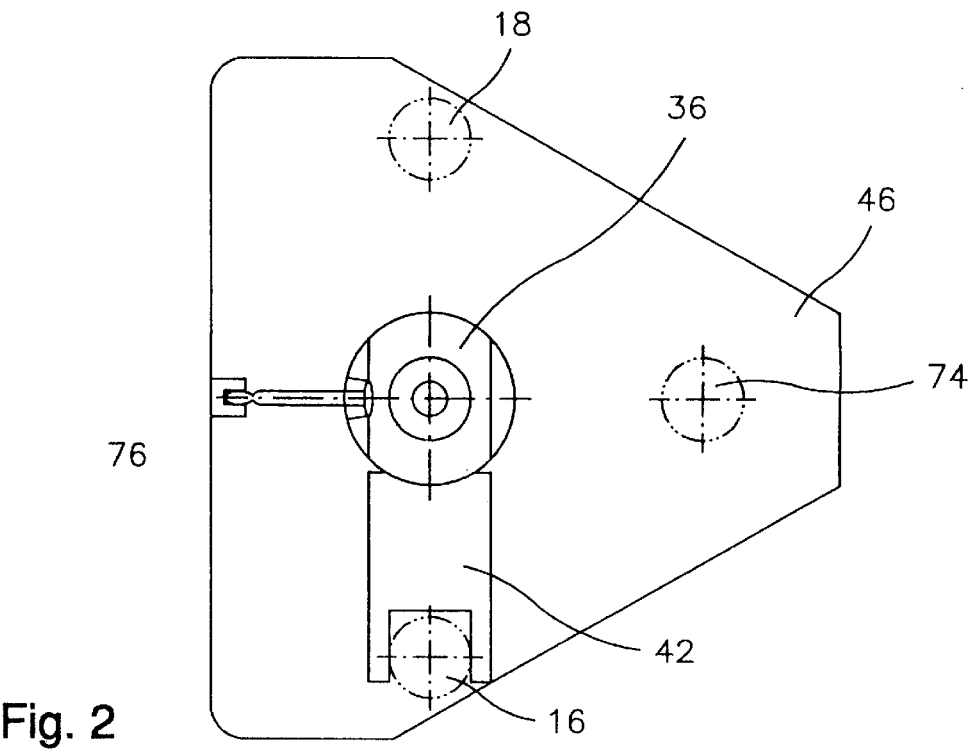
FIG. 2 shows a bottom view in the direction of arrow II—II of FIG. 1 representing the unit receiving the drive and the pressure sensing device.

In order to prevent rotation of the sleeve 36 upon actuating the step motor 22, a rotational stop 42 is provided which, as can be seen in FIG. 2, surrounds the pull element 18 in a substantially U-shaped manner so that a rotation of the sleeve 36 is prevented. The pull element 18 is comprised preferably of polished steel and the stop 42 can glide substantially without play and thus with minimal friction thereat, whereby the stop 42 is securely attached to the sleeve 36.

The drive 20 is received together with the pressure sensing device PSD in the pre-assembled unit 44. The unit 44 extends from the counter plate 30 to the support plate 46 whereby the two plates 30 and 46 are supported at one another by two support rods two of which, 50 and 52, are shown in FIG. 1.

Preferably, the support rods 50 and 52 are embodied as threaded rods secured by lock nuts so that the spacing between the counter plate 30 and the support plate 46 can be adjusted. The support plate 46 has a central cutout 60 in which the projection 62 of the step motor 22 is received. A flange 64 of the step motor 22 surrounds the projection 62 and is supported at the support plate 46 so that upon loading by the counter force of the piston 14 the step motor 22 is slightly removed from the support plate 46 but is securely guided in the cutout 60 while the deformation element 28 is compressed.

As can be seen in FIG. 1, the unit 44 is fastened with threaded bolts 70, 72 to the pull elements 16 and 18 in the form of pull rods. This arrangement together with the embodiment of the sleeve 36 placed on the piston 14 allows a subsequent assembly of the inventive drive unit 44 which can be correspondingly pre-assembled and adjusted before it is mounted on the furnace. Preferably, the spacing between the support plate 46 and the counter plate 30 is such that the step motor 22 presses slightly onto the deformation member 28 without compressing it to a noticeable extent. This position corresponds to the zero loading of the pressure sensing device PSD which is electrically connected to a non-represented a control circuit for the step motor and the furnace.

FIG. 2 shows that instead of the two pull elements 16 and 18 shown in FIG. 1 a total of three such pull elements 16, 18, 74 arranged on the corners of a triangle can be realized. Identical reference numerals referred to same parts in the Figures so that no additional explanation is required for the parts. The support plate 46 in the shown embodiment is substantially triangular whereby it is understood that any other suitable guide can be employed without leaving the gist of the invention.

FIG. 2 shows also the arrangement of a travel sensor 76 which operates based on a potentiometer or by optical encoding and is fastened to the sleeve 36.

Figure 3:
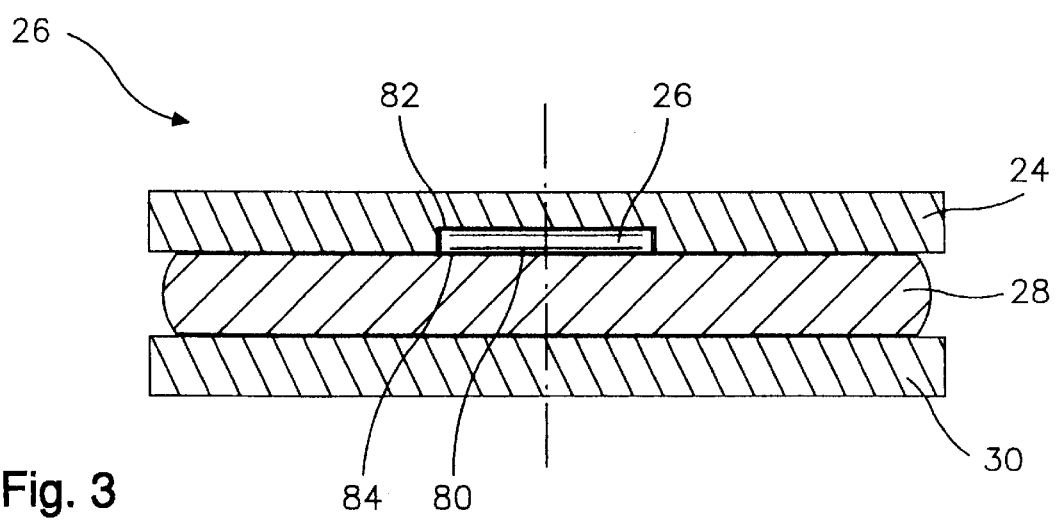
FIG. 3 shows an enlarged representation of the pressure sensing device of the embodiment according to FIG. 1.

FIG. 3 shows the design of the pressure sensing device PSD. The counter plate 30 is secured by the deformation member 28 at a spacing from the sensor plate 24. The sensor plate 24 comprises a central cutout 80 having a surface area corresponding to $\frac{1}{10}$ of the surface area of the sensor plate 24 and corresponding in its dimensions to the actual pressure sensor 26 received therein. The pressure sensor 26 has two spaced apart plates as sensor elements 82, 84. The change in distance between the sensor elements is then transformed into electric signals as is known in the prior art. An example for such a pressure sensor 26 is a piezoelement or a capacitive pressure sensor.

Upon compression of the sensor plate 24 and of the counter plate 30, the deformation member 28 is compressed. Due to the elastic properties of the deformation member 28 it thus substantially uniformly applies pressure across its entire surface area and thus also onto the pressure sensor 26.

Since the greater portion of the surface area of the deformation member 28 rests at the sensor plate 24 and not at the pressure sensor 26, the supporting action is thus distributed over substantially large portions directly between the sensor plate 24 and the deformation member 28. A proportional smaller force is thus received by the pressure sensor 26 so that for an increasing pressure it will emit a correspondingly greater output signal.

It is understood that the pressure sensing device PSD comprised of sensor plate 24, counter plate 30, deformation member 28, and pressure sensor 26 is already calibrated. For this purpose, it is possible to apply for a short period of time an increasing and known force, to plot this force as a function of the usually non-linear output signal of the piezoelement and save the results so that the corresponding measured values can be entered directly into the electronic control circuit for the step motor.

It is understood that instead of the piezoelement any other suitable force uptake, for example, strain gauge elements can be used. It should be noted that even for a strain gauge element a systematic non-linearity can be compensated by performing a calibration step and saving the calibration results.

While the inventive support of the sensor element 84 at the muffle furnace is preferably ensured by supporting the sensor element 84 at the counter plate 30, which is connected fixedly by the pull elements to the bottom plate for the muffle, it is understood that an indirect support at the muffle furnace is also possible in which the pull elements are connected to the pivotable furnace hood which, during firing, is in a defined position relative to the muffle.

Figure 4:
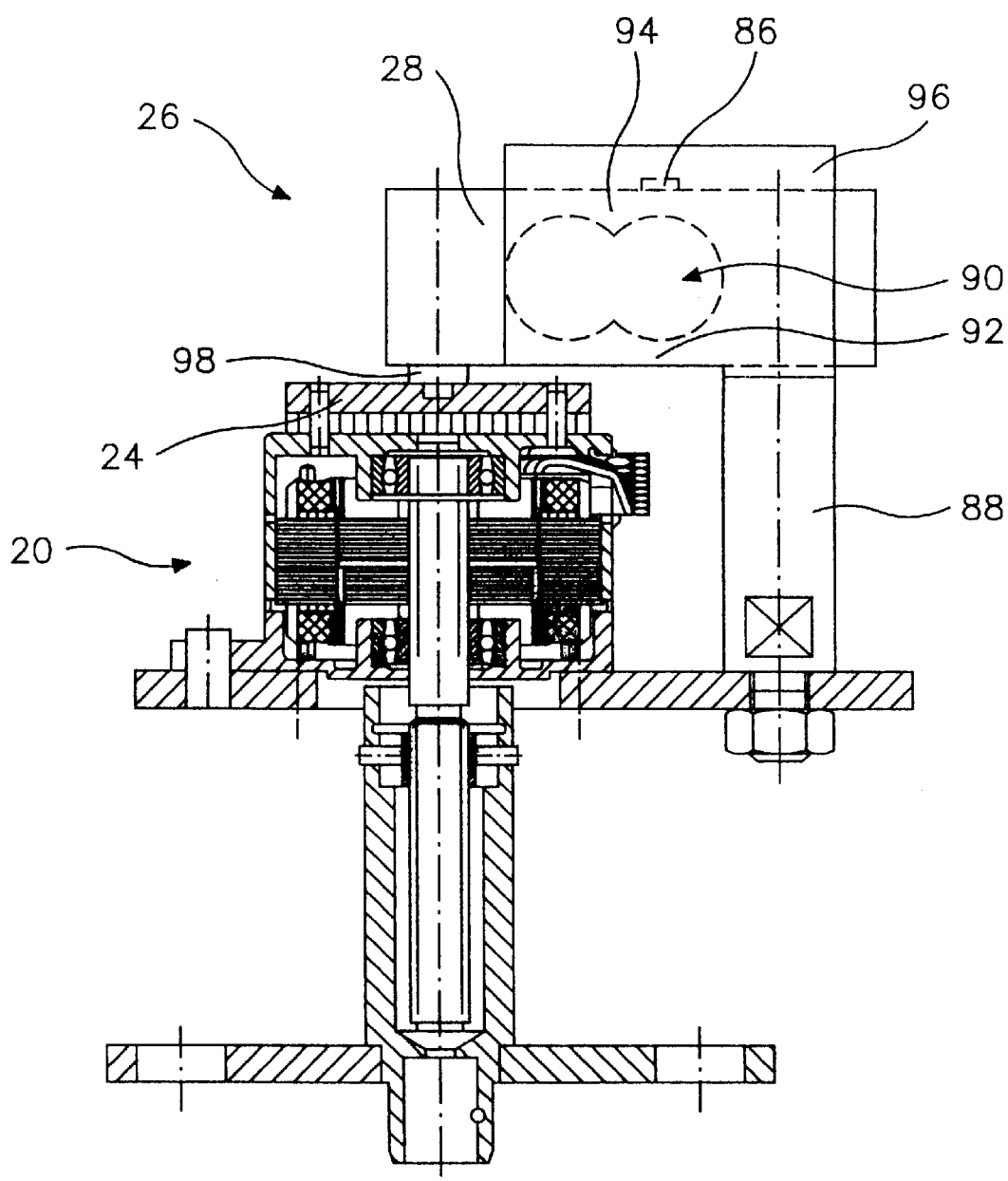
FIG. 4 shows a representation of a further embodiment of a portion of the inventive furnace.

The embodiment according to FIG. 4 shows a modified design of the inventive furnace which is especially preferred. In this embodiment the pressure sensing device PSD comprises a deformation member 28 which is embodied as a bending bar having on one surface thereof a strain gauge 86. The bending bar 28 is securely fastened to a support 88 which is itself fixedly connected to the muffle furnace.

The bending bar is comprised in the shown embodiment of aluminum and has a central cutout 90 which separates a pull leg 92 and a pressure leg 94 from one another. The cutout 90 and the corresponding legs 92, 94 are shown in dashed lines in FIG. 4 because a cover 96 covers this sensitive area including the strain gauge 86.

The drive 20 is connected to the deformation member 28 at the end adjacent to the pull leg 92 and supported on the support 88. For centering, a mandrel 98 is provided at the deformation member 28 which is supported in the shown embodiment at the sensor plate 24 which is a pressure plate.

Despite this one-sided support action, the represented embodiment allows for an especially precise detection of the advancing force without being subject to fatigue. This embodiment is especially suitable for low viscosity ceramics to be pressed with short residence time of the ceramic in the embedding material.

The present invention is, of course, in no way restricted to the specific disclosure of the specification and drawings, but also encompasses any modifications within the scope of the appended claims.

What is claimed is:

1. A muffle furnace for producing dental prostheses, said furnace comprising:
   a muffle (12) into which dental material is placed;
   a drive (20);
   a piston (14) connected to said drive (20);
   said piston (14) moveable by said drive (20) into said muffle (12) to apply pressure onto the dental material;
   a pressure sensing device (PSD) for measuring pressure onto the dental material;
   said pressure sensing device (PSD) comprising a pressure sensor (26) and a deformation member (28) having a first side and a second side;
   wherein said first side of said deformation member (28) is subjected to a counter force of said piston (14) and wherein said second side of said deformation member (28) is fixedly attached to said muffle furnace.

2. A muffle furnace according to claim 1, wherein said piston (14) has a distal end face facing away from said muffle (12) and wherein said first side of said deformation member (28) is facing said distal end face of said piston (14).

3. A muffle furnace according to claim 1, wherein said pressure sensor (26) measures a pressure applied onto said piston (14).

4. A muffle furnace according to claim 1, wherein said piston (14) has a distal end face facing away from said muffle (12) and wherein said pressure sensor (26) is positioned between said distal end face of said piston (14) and said muffle furnace.

5. A muffle furnace according to claim 1, wherein said deformation member (28) encloses said pressure sensor (26) at least on two sides.

6. A muffle furnace according to claim 1, wherein said deformation member (28) annularly surrounds said pressure sensor (26).

7. A muffle furnace according to claim 1, wherein said drive (20) comprises a step motor (22) and wherein said pressure sensor (26) sends a signal for controlling said step motor (22).

8. A muffle furnace according to claim 1, wherein said drive (20) has a maximum driving force limited to a value below a maximum deformation force of the dental material, wherein said drive (20) emits a warning signal when the maximum driving force is reached.

9. A muffle furnace according to claim 8, wherein said drive (20) is switched off when said maximum driving force is reached.

10. A muffle furnace according to claim 1, wherein said drive (20) comprises a step motor (22) and a control circuit, wherein said control circuit sends actuating signals to said step motor when said pressure sensor (26) detects a driving force of said step motor (22) that is below a set point driving force of said step motor (22).

11. A muffle furnace according to claim 10, wherein said pressure sensor (26) has an output terminal connected to said control circuit and wherein said control circuit controls an advancing speed of said piston (14) based on piston travel or pressure or a combination of piston travel and pressure.

12. A muffle furnace according to claim 1, wherein said deformation member (28) is thermally decoupled from a heating area of said muffle furnace.

13. A muffle furnace according to claim 12, further comprising a sintered ceramic plate having minimal heat conducting properties, wherein said sintered ceramic plate is positioned between said deformation member (28) and said piston (14).

14. A muffle furnace according to claim 1, wherein said piston (14) comprises a ceramic rod extending into said muffle (12).

15. A muffle furnace according to claim 1, wherein said drive (20) comprises a threaded spindle (32) and wherein said piston (14) comprises a sleeve (36) having an inner thread extending at least over a portion of a length of said sleeve (36), wherein said threaded spindle (32) engages said inner thread.

16. A muffle furnace according to claim 15, wherein said sleeve (36) comprises a nut (34) and wherein said inner thread is located within said nut (34).

17. A muffle furnace according to claim 1, further comprising a bottom plate for placing said muffle (12) thereon and pull elements (16, 18, 74) connected to said bottom plate, wherein said drive (20) is a compact drive unit (44) arranged axially at an end of said piston (14) remote from said muffle (12) and wherein said drive (20) is connected by said pull elements (16, 18, 74) to said bottom plate.

18. A muffle furnace according to claim 1, wherein said drive (20) comprises a motor and a control circuit, wherein said control circuit receives a signal form said pressure sensor (26) and controls said motor so as to change the pressure measured by said pressure sensor (26).

19. A muffle furnace according to claim 1, wherein said drive (20) comprises a motor and a control circuit, wherein said control circuit receives a signal form said pressure sensor (26) and controls said motor so as to change a pressing rate.

20. A muffle furnace according to claim 1, wherein said drive (20) comprises a motor and a control circuit, wherein said control circuit takes into account elastic properties of said piston (14) for determining a pressure force to be supplied at a pressure applying end of said piston (14).

21. A muffle furnace according to claim 1, further comprising a travel sensor (76) connected to said piston (14).

22. A muffle furnace according to claim 21, wherein said drive (20) comprises a step motor (22), wherein said travel sensor (76) employs advancing signals of said step motor (22) for determining travel.

23. A muffle furnace according to claim 1, wherein said first side of said deformation member (28) rests at said piston (14) or at said drive (20).

24. A muffle furnace according to claim 1, wherein said first side of said deformation member (28) is part of said piston (14).

25. A muffle furnace according to claim 1, wherein said deformation member (28) is L-shaped having a first leg and a second leg, wherein said pressure sensor (26) is connected to said first leg and wherein said drive (20) rests one a tip of said first leg.

26. A muffle furnace according to claim 1, comprising a support (88) fixedly attached to said muffle furnace, wherein said deformation member (28) is fastened to said support (88).

27. A muffle furnace according to claim 1, wherein said deformation member (28) is embodied as a bending bar comprising a wire strain gauge (86) connected to one side of said bending bar.

28. A muffle furnace according to claim 27, wherein said bending bar has a cutout (90) extending over half a length of said bending bar and over about $\frac{2}{3}$ of a width of said bending bar.

29. A muffle furnace according to claim 1, wherein said deformation member (28) consists of metal.

30. A muffle furnace according to claim 1, wherein said deformation member (28) consists of aluminum or an aluminum alloy.

* * * * *